United States Patent
Heshmati et al.

(10) Patent No.: US 9,855,294 B2
(45) Date of Patent: Jan. 2, 2018

(54) METHODS FOR TREATING OVERWEIGHT OR OBESITY

(71) Applicant: Gelesis, LLC, Boston, MA (US)

(72) Inventors: Hassan Heshmati, Anthem, AZ (US); Eyal S. Ron, Lexington, MA (US); Alessandro Sannino, Lecce (IT); Yishai Zohar, Boston, MA (US)

(73) Assignee: Gelesis, LLC, Boston, MA (US)

( * ) Notice: Subject to any disclaimer, the term of this patent is extended or adjusted under 35 U.S.C. 154(b) by 10 days.

(21) Appl. No.: 14/744,506

(22) Filed: Jun. 19, 2015

(65) Prior Publication Data

US 2015/0366898 A1 Dec. 24, 2015

Related U.S. Application Data

(60) Provisional application No. 62/014,926, filed on Jun. 20, 2014.

(51) Int. Cl.
*A61K 31/738* (2006.01)

(52) U.S. Cl.
CPC .................. *A61K 31/738* (2013.01)

(58) Field of Classification Search
None
See application file for complete search history.

(56) References Cited

U.S. PATENT DOCUMENTS

| | | |
|---|---|---|
| 3,526,048 A | 9/1970 | Rowland et al. |
| 4,697,008 A | 9/1987 | Asano et al. |
| 5,137,537 A | 8/1992 | Herron et al. |
| 5,247,072 A | 9/1993 | Ning et al. |
| 5,415,864 A | 5/1995 | Kopecek et al. |
| 5,550,189 A | 8/1996 | Qin et al. |
| 5,800,418 A | 9/1998 | Ahr |
| 5,873,979 A | 2/1999 | Naieni |
| 6,271,278 B1 | 8/2001 | Park et al. |
| 6,471,824 B1 | 10/2002 | Jewell |
| 6,630,422 B1 | 10/2003 | Sannino et al. |

(Continued)

FOREIGN PATENT DOCUMENTS

| | | |
|---|---|---|
| DE | 212 969 | 8/1984 |
| DE | 196 54 745 A1 | 7/1998 |

(Continued)

OTHER PUBLICATIONS

Diseases & Conditions: Diabetes, Prevention, (Cleveland Clinic), p. 1-2, 2013, [retrieved on Aug. 14, 2015].

(Continued)

*Primary Examiner* — Shaojia Anna Jiang
*Assistant Examiner* — Dale R Miller
(74) *Attorney, Agent, or Firm* — Edgar W. Harlan; Carolyn S. Elmore; Elmore Patent Law Group, P.C.

(57) ABSTRACT

The present invention relates to methods of managing weight, and treating overweight or obesity and treating or preventing diabetes in a subject in need thereof. In one embodiment, the method comprises the steps of (a) orally administering to the subject from about 0.7 g to about 4 g of crosslinked carboxymethylcellulose; and (b) orally administering to the subject at least about 100 mL of water per gram of crosslinked carboxymethylcellulose. Steps (a) and (b) are conducted prior to or with at least one meal per day.

12 Claims, 11 Drawing Sheets

(56) References Cited

U.S. PATENT DOCUMENTS

| | | |
|---|---|---|
| 6,765,042 B1 | 7/2004 | Thornton et al. |
| 7,071,327 B2 | 7/2006 | Mensitieri et al. |
| 8,658,147 B2 | 2/2014 | Sannino et al. |
| 2001/0006677 A1 | 7/2001 | McGinity et al. |
| 2002/0146495 A1 | 10/2002 | Loh et al. |
| 2004/0192582 A1 | 9/2004 | Burnett et al. |
| 2005/0100603 A1 | 5/2005 | Sako et al. |
| 2005/0118326 A1 | 6/2005 | Anfinsen et al. |
| 2005/0143571 A1 | 6/2005 | Stoyanov et al. |
| 2006/0102483 A1 | 5/2006 | Chuang et al. |
| 2006/0286264 A1 | 12/2006 | Don et al. |
| 2008/0070997 A1 | 3/2008 | Takigami et al. |
| 2008/0095911 A1 | 4/2008 | Adams et al. |
| 2008/0227944 A1 | 9/2008 | Ambrosio et al. |
| 2008/0241094 A1 | 10/2008 | Burnett et al. |
| 2009/0311235 A1 | 12/2009 | Elenko et al. |
| 2009/0324537 A1 | 12/2009 | Bucevschi et al. |
| 2010/0234233 A1 | 9/2010 | Sannino et al. |
| 2010/0273704 A1* | 10/2010 | Korsmeyer ........ A61K 38/1761 514/7.3 |
| 2012/0052151 A1 | 3/2012 | Sannino et al. |
| 2013/0089737 A1 | 4/2013 | Sannino et al. |
| 2014/0296507 A1 | 10/2014 | Sannino et al. |
| 2015/0196641 A1 | 7/2015 | Elenko et al. |

FOREIGN PATENT DOCUMENTS

| | | | |
|---|---|---|---|
| EP | 0471558 A2 | 8/1991 | |
| JP | 01-187048 | 7/1989 | |
| JP | 2008069315 | 3/2008 | |
| WO | 9602276 A2 | 2/1996 | |
| WO | 9926670 A1 | 6/1999 | |
| WO | 0032064 A1 | 6/2000 | |
| WO | 0187365 A2 | 11/2001 | |
| WO | 2006069422 A1 | 7/2006 | |
| WO | 2006070337 A2 | 7/2006 | |
| WO | 2007013794 A1 | 2/2007 | |
| WO | 2007112436 | 10/2007 | |
| WO | 2007115169 | 10/2007 | |
| WO | WO 2007115169 A2 * | 10/2007 | ........... A61K 9/0065 |
| WO | 2009021701 | 2/2009 | |
| WO | 2009022358 | 2/2009 | |

OTHER PUBLICATIONS

Demitri, C., et al., "Novel Superabsorbent Cellulose-Based Hydrogels Crosslinked with Citric Acid," Journal of Applied Polymer Science, 110:2453-2460 2008.
Esposito, F., et al., "Water Sorption in Cellulose-Based Hydrogels," Journal of Applied Polymer Science, 60:2403-2407, 1996.
Qiu, et al., "Effect of activated carbon on the properties of carboxymethylcellulose/activated carbon hybrid synthesized hydrogels by γ-radiation techniqu", Carbohydrate Polymers, 70:236-242, 2007.
Ogushi, et al., "Synthesis of Enzymatically-Gellable Carboxymethylcellulose for Biomedical Applications," Journal of Bioscience and Bioengineering, 104(1):30-33, 2007.
Liu, et al., "Radiation crosslinking of CMC-Na at low dose and its application as substitute for hydrogel," Radiation Physics and Chemistry, 72:635-638, 2005.
Liu, et al., "Radiation preparation and swelling behavior of sodium carboxymethyl cellulose hydrogels," Radiation Physics and Chemistry, 63:525-528, 2002.
Gorgieva, et al., "Synthesis and application of new temperature-responsive hydrogels based on carboxymethyl and hydroxyethyl cellulose derivatives for the functional finishing of cotton knitwear," Carbohydrate Polymers, 85:664-673, 2011.
Ito, "The prevention of peritoneal adhesions by in situ cross-linking hydrogels of hyaluronic acid and cellulose derivatives," Biomaterials, 28:975-983, 2007.
Chang, et al., "Superabsorbent hydrogels and based on cellulose for smart swelling and controllable delivery," European Polymer Journal, 46:92-100, 2010.

Chang, et al., "Structure and properties of hydrogels prepared from cellulose in NaOH/urea aqueous solutions," Carbohydrate Polymers, 82:122-127, 2010.
Esposito, et al., "Response of intestinal cells and macrophages to an orally administered cellulose-PEG based polymer as a potential treatment for intractable edemas," Biomaterials, 26:4101-4110, 2005.
Sannino, et al., "Cellulose-based hydrogels as body water retainers," J. Mater Sci: Mat in Med., 11:247-253, 2000.
Sannino, et al., "Spin Coating Cellulose Derivatives on Quartz Crystal Microbalance Plates to Obtain Hydrogel-Based Fast Sensors and Actuators," Journal of Applied Polymer Sci., 106:3040-3050, 2007.
Sannino, et al., "Concurrent effect of microporosity and chemical structure on the equilibrium sorption properties of cellulose-based hydrogels," Polymer, 46:4676-4685, 2005.
Sannino, et al., "Water and Synthetic Urine Sorption Capacity of Cellulose-Based Hydrogels under a Compressive Stress Field," Journal of Applied Polymer Science, 91:3791-3796, 2004.
Casciaro, et al., "Full experimental modelling of a liver tissue mimicking phantom for medical ultrasound studies employing different hydrogels," J. Mater Sci: Mater Med, 20:983-989, 2009.
Sannino, et al., "Designing microporous macromolecular hydrogels for biomedical applications: a comparison between two techniques," Composites Science and Technology, 63:2411-2416, 2003.
Lionetto, et al., "Ultrasonic monitoring of the network formation in superabsorbent cellulose based hydrogels," Polymer, 46:1796-1803, 2005.
Sannino, et al., "Development and Characterization of Cellulose-Based Hydrogels for Use as Dietary Bulking Agents," Journal of Applied Polymer Science, 115:1438-1444, 2010.
Marci, et al., "Environmentally sustainable production of cellulose-based superabsorbent hydrogels," Green Chem., 8:439-444, 2006.
Sannino, et al., "A Cellulose-Based Hydrogel as a Potential Bulking Agent for Hypocaloric Diets: An In Vitro Biocompatibility Study on Rat Intestine," Journal of Applied Polymer Science, 102:1524-1530, 2006.
Sannino, et al., "Crosslinking of cellulose derivatives and hyaluronic acid with water-soluble carbodiimide," Polymer, 46:11206-11212, 2005.
Sannino, et al., "Cellulose Derivative-Hyaluronic Acid-Based Microporous Hydrogels Cross-Linked through Divinyl Sulfone (DVS) to Modulate Equilibrium Sorption Capacity and Network Stability," Biomacromolecules, 5:92-96, 2004.
Sannino, et al., "Biomedical application of a superabsorbent hydrogel for body water elimination in the treatment of edemas," J. Biomed. Mater Res., 67A:1016-1024, 2003.
Sannino, et al., "Introduction of Molecular Spacers Between the Crosslinks of a Cellulose-Based Superabsorbent Hydrogel: Effects on the Equilibrium Sorption Properties," Journal of Applied Polymer Science, 90:168-174, 2003.
Demitri, et al., "Hydrogel Based Tissue Mimicking Phantom for In-Vitro Ultrasound Contrast Agents Studies", J. Biomed Mater Res Part B: Appl Biomater, 87B:338-345, 2008.
Lenzi, et al., "Probing the degree of crosslinking of a cellulose based superabsorbing hydrogel through traditional and NMR techniques," Polymer, 44:1577-1588, 2003.
Capitani, et al., "13C Solid-State NMR Determination of Cross-Linking Degree in Superabsorbing Cellulose-Based Networks," Macromolecules, 33:430-437, 2000.
Sannino, et al, "Biodegradable-Cellulose-based Hydrogels: Design and Applications," Materials, 2:353-373, 2009.
Coma, et al., "Film properties from crosslinking of cellulosic derivatives with a polyfunctional carboxylic acid," Carbohydrate Polymers, 51:265-271, 2003.
Anbergen, et al., "Elasticity and swelling behaviour of chemically crosslinked cellulose ethers in aqueous systems*," Polymer, 31:1854-1858, 1990.
Casciaro, et al., "Experimental investigation and theoretical modelling of the nonlinear acoustical behaviour of a liver tissue and comparison with a tissue mimicking hydrogel," J. Mater Sci: Mater Med, 19:899-906, 2008.

(56) References Cited

OTHER PUBLICATIONS

Eckel, R.H., "Obesity and Heart Disease: A Statement for Healthcare Professionals from the Nutrition Committee," American Heart Association, 96:3248-3250, 1997.

Xie, et al., "Development and Physicochemical Characterization of New Resistant Citrate Starch from Different Corn Starches," Starch, 56:364-270, 2004.

\* cited by examiner

METHODS FOR TREATING OVERWEIGHT OR OBESITY

RELATED APPLICATION

This application claims the benefit of U.S. Provisional Application No. 62/014,926, filed on Jun. 20, 2014. The entire teachings of the above application are incorporated herein by reference.

BACKGROUND OF THE INVENTION

Public health efforts and current anti-obesity agents have not controlled the obesity epidemic. This disorder is increasingly prevalent in industrialized nations because of the abundance of food and the reduced activity levels that accompany the movement of populations from rural to urban settings. Obesity is loosely defined as an excess of body fat over that needed to maintain health.

Obesity is a condition in which excess body fat has accumulated to such an extent that health may be negatively affected. (World Health Organization (2000)). (Technical report series 894: Obesity: Preventing and managing the global epidemic). It is commonly defined as a Body Mass Index (BMI=weight divided by height squared) of 30 kg/m$^2$ or higher. Overweight is distinguished and defined as a BMI between 25-29.9 kg/m$^2$ (Obes Res. 1998 September; 6 Suppl 2:51S-209S. (Clinical Guidelines on the Identification, Evaluation, and Treatment of Overweight and Obesity in Adults—The Evidence Report. National Institutes of Health).

Excessive body weight is associated with various diseases, particularly cardiovascular diseases, diabetes mellitus type 2, obstructive sleep apnea, certain types of cancer, and osteoarthritis (National Heart, Lung, and Blood Institute. Clinical Guidelines on the Identification, Evaluation, and Treatment of Overweight and Obesity in Adults NIH Publication No. 98-4083 September 1998 National Institutes of Health). As a result, obesity has been found to reduce life expectancy. The primary treatment for obesity is dieting and physical exercise. If diet and exercise fails, anti-obesity drugs and bariatric surgery may be recommended in severe cases (National Institute for Health and Clinical Excellence. Clinical Guideline 43: Obesity: The prevention, identification, assessment and management of overweight and obesity in adults and children. London, 2006).

The pathogenesis of obesity is multi-factorial and includes the control of feeding behavior, mechanisms of fat storage, the components of energy intake and expenditure, and genetic and psychological influences. Likewise, the treatment of obesity is generally multi-factorial. Unfortunately, the mechanisms of fat storage and genetic influences are not, generally speaking, amenable to treatment. Moreover, the control of feeding behavior and psychological influences require prolonged treatment. Although the components of energy intake and expenditure are treatable, many obese individuals are resistant to or incapable of engaging in activities which significantly increase their energy expenditure. Therefore, controlling energy intake is an attractive approach for the treatment of obesity.

There is a need for new methods for managing weight and preventing or treating overweight and obesity. Further, treatments for obesity are typically no more effective in diabetic patients than in nondiabetic patients and are often less effective (see, for example: Baker et al., Met. Clin. Exper. 2012, 61:873; Scheen et al., Lancet 2006, 368:95489, 1660; Pi-Sunyer et al., J. Am. Med. Assoc. 2006, 295:7, 761; Khan et al., Obes. Res. 2000, 8:1, 43; Guare et al., Obes. Res. 1995, 3:4, 329; Wing et al., Diabetes Care 1987, 10:5, 563). Thus there is a need for weight loss agents and methods which are particularly effective in treating diabetic patients. In addition, there is a need for effective methods for weight loss in prediabetics and for improving their health even in the absence of weight loss, for example, converting prediabetics to nondiabetics.

SUMMARY OF THE INVENTION

The present invention relates to methods of inducing weight loss, managing weight, and treating overweight or obesity and treating or preventing diabetes in a subject in need thereof. In one embodiment, the method comprises the steps of (a) orally administering to the subject from about 0.7 g to about 4 g of crosslinked carboxymethylcellulose; and (b) orally administering to the subject at least about 100 mL of water per gram of crosslinked carboxymethylcellulose. Steps (a) and (b) are conducted prior to or with at least one meal per day.

In another embodiment, the invention provides a method for treating or preventing diabetes or improving glycemic control in a subject. The method comprises orally administering to the subject from about 0.7 g to about 4 g of crosslinked carboxymethylcellulose. This method is conducted prior to or with at least one meal per day.

DETAILED DESCRIPTION OF THE INVENTION

Figure 1:
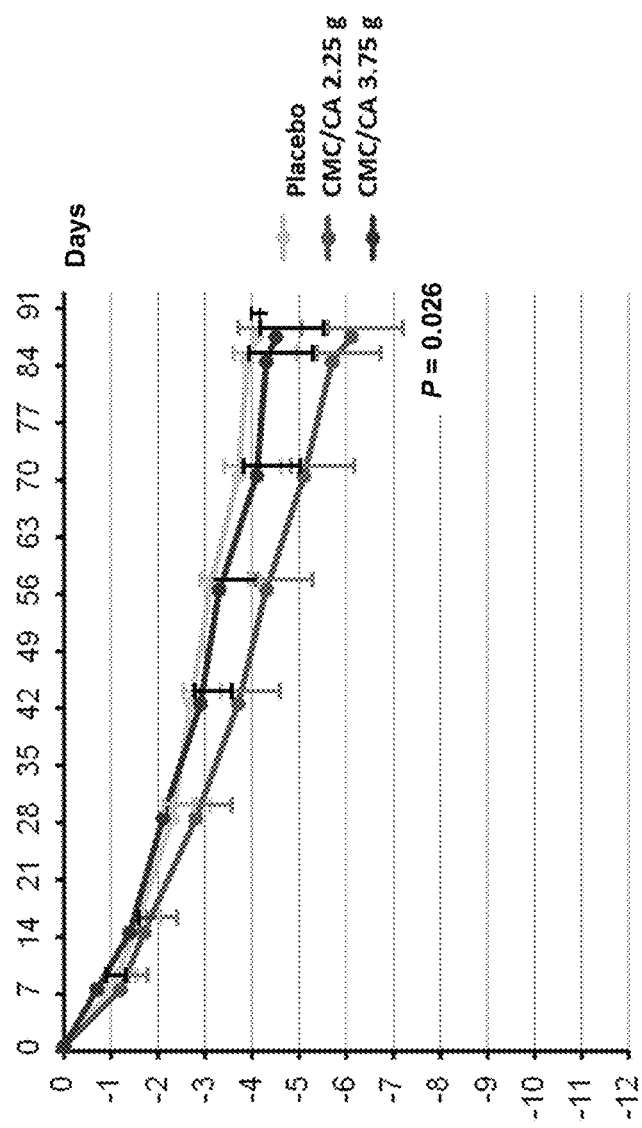
FIG. 1 is a graph showing the change in body weight (% change from baseline, mean±SEM) for the placebo, CMC/CA 2.25 g and CMC/CA 3.75 g groups over the course of the study described in Example 2.

The methods of the invention are of use in inducing weight loss, maintaining weight, treating or preventing diabetes and/or improving glycemic control in a subject in need thereof. In particular, the methods of the invention are useful for inducing weight loss in subjects having elevated fasting blood glucose levels prior to treatment, prediabetic subjects and diabetic subjects. In certain embodiments, the methods are useful for lowering the fasting blood glucose of a subject from a level indicative of prediabetes to a normal level.

Methods for Inducing Weight Loss

In one embodiment, the invention provides a method for inducing weight loss in an overweight or obese subject, particularly in subjects having elevated fasting blood glucose levels, prediabetic subjects and diabetic subjects.

The method can be used to treat obesity or overweight. The method can also be used to manage or maintain weight, i.e., prevent or inhibit weight gain, in a subject who is of normal weight or is overweight. The present methods are particularly effective in inducing weight loss in prediabetic and diabetic subjects.

In one embodiment, the method of the invention for inducing weight loss comprises the steps of (a) orally administering to the subject from about 0.7 to 4 g of crosslinked carboxymethylcellulose; and (b) orally administering to the subject at least about 100 mL of water per gram of crosslinked carboxymethylcellulose. In one embodiment, method steps (a) and (b) are conducted prior to or with at least one meal per day. In certain embodiments, method steps (a) and (b) are conducted prior to or with two meals per day. In certain embodiments, method steps (a) and (b) are conducted prior to or with three meals per day. In certain embodiments, the subject is directed to eat four or more meals per day, and method steps (a) and (b) are conducted prior to or with at least one meal per day, at least two meals per day, at least 3 meals per day or at least 4 meals per day. In other embodiments, steps (a) and (b) are conducted prior to or with every meal of the day.

The method of the invention is preferably conducted daily for a period of days sufficient to achieve a significant weight loss. For example, the method can be conducted daily until a desired or beneficial amount of weight loss. In certain embodiments, the treatment is continued until the subject has lost a predetermined amount of weight. Preferably, the subject has lost 3 to 20% of his or her initial body weight, preferably at least 5%. In one embodiment, the method is conducted daily until the subject has lost from 5 to 15% of his or her initial body weight. For example, the method can be conducted daily up to one week, up to four weeks, up to eight weeks, up to twelve weeks, up to sixteen weeks, up to twenty weeks, up to twenty-four weeks, up to 36 weeks, or up to one year or longer. In some embodiments, the method is conducted chronically, i.e., for a period of greater than one year or for an indefinite period. In some embodiments, the method is conducted daily for a first period of time, stopped for a second period and then conducted for a third period of time. This alternation of treatment periods and nontreatment periods can be conducted over multiple cycles or continued indefinitely.

In one embodiment, the amount of crosslinked carboxymethylcellulose administered in step (a) is from about 0.7 g to about 4 g, or about 0.7 g to about 3 g. In certain embodiments, the amount of crosslinked carboxymethylcellulose administered in step (a) is from about 1.1 g to about 3 g, from about 1.5 g to about 3.0 g, from about 1.8 g to about 3.0 g or from about 1.75 g to about 2.75 g. In certain embodiments, the amount of crosslinked carboxymethylcellulose is from 1.9 to 2.5 g or 2.0 to 2.5 g. In certain embodiments, the amount of crosslinked carboxymethylcellulose is from 2.0 to 2.35 g or 2.15 to 2.35 g. In certain embodiments, the amount of crosslinked carboxymethylcellulose is about 2.25 g.

The amount of water administered in step (b) is preferably at least about 100 mL per gram of crosslinked carboxymethylcellulose, and is more preferably at least about 150 mL per gram of crosslinked carboxymethylcellulose. In certain embodiments, the amount of water administered is from about 150 mL to about 250 mL per gram of crosslinked carboxymethylcellulose. In certain embodiments the amount of water administered is at least about 175 mL per gram of crosslinked carboxymethylcellulose. In other embodiments, the amount of water administered at least about 200 mL per gram of crosslinked carboxymethylcellulose. In certain embodiments, the amount of water administered is at least about 400 mL. In certain embodiments, the amount of water administered is at least about 450 mL, 475 mL or 500 mL to 550 mL.

Although there is no upper limit on the amount of water to be administered, preferably the amount of water administered and/or the rate at which the water is consumed does not cause the subject discomfort.

Method steps (a) and (b) are preferably conducted at a time prior to or concurrently with the meal which is sufficient for significant swelling of the crosslinked carboxymethylcellulose in the stomach of the subject. In one embodiment, step (a) is conducted from 0 to 50 minutes prior to the meal. In another embodiment, step (a) is conducted from 15 to 40 minutes prior to the meal. Preferably, step (a) is conducted from 20 to 30 minutes prior to the meal. In one embodiment, step (b) is conducted from 0 to 20 minutes after step (a). In another embodiment, step (b) is conducted from 3 to 15 minutes after step (a). Preferably, step (b) is conducted from about 3 to about 10 minutes or 3 to 7 minutes after step (a). In one embodiment, step (b) is begun simultaneously with step (a) and administration of water can continue for period of time sufficient for the subject to comfortably consume the water and can continue into the meal, for example, until halfway through the meal.

The present method of treatment is optionally administered in combination with a hypocaloric diet, i.e., a diet providing fewer than the required calories for the subject. The estimated caloric requirement for a given subject can be determined using methods known in the art and will depend on factors such as gender, age and weight. In one embodiment, the hypocaloric diet provides fewer than 2000 kcal of energy per day. Preferably, the hypocaloric diet provides from 1200 to 2000 kcal per day. In one embodiment, the subject consumes a diet which provides a deficit of at least 100, 200, 300, 400, 500 or 600 kcal per day. A hypocaloric diet can be administered temporarily or throughout the course of treatment.

In one embodiment, steps (a) and (b) are conducted prior to or with one meal per day and the daily amount of crosslinked carboxymethylcellulose is from about 1.1 g to about 2.25 g. In one embodiment, steps (a) and (b) are conducted prior to or with two meals per day and the daily amount of crosslinked carboxymethylcellulose is from about 1.1 g to about 4.5 g, preferably from about 2.2 g to 4.5 g. In one embodiment, steps (a) and (b) are conducted prior to or with three meals per day and the daily amount of crosslinked carboxymethylcellulose is from about 1.65 g to about 6.75 g, preferably from about 3.3 g to about 6.75 g. In one embodiment, steps (a) and (b) are conducted prior to or with four meals per day and the daily amount of crosslinked carboxymethylcellulose is from about 2.2 g to about 6 g or 2.2 g to about 9 g, preferably from about 4.4 g to about 6 g or 4.4 g to about 9 g.

In another embodiment, the method of the invention is useful for maintaining a desired weight, for example, by inhibiting weight gain by a subject. In one embodiment, the subject has lost weight using the method of the invention and is then placed on a maintenance dose of the crosslinked carboxymethylcellulose. The subject can be of normal weight or overweight, but susceptible to weight gain. In certain embodiments, the amounts of crosslinked carboxymethylcellulose and water administered and the frequency of administration are as described above. In another embodiment, the amount of crosslinked carboxymethylcellulose administered is lower and/or is administered fewer times per day compared to use of the method to induce weight loss. In certain embodiments, the method is conducted prior to or with one meal per day. In another embodiment, the amount of crosslinked carboxymethylcellulose administered is step (a) is from about 0.7 g to about 2.0 g. The amount of water administered in step (b) is at least about 100 mL per gram of crosslinked carboxymethylcellulose. In certain embodiments the amount of water is at least about 125 mL or at least about 150 mL per gram of crosslinked carboxymethylcellulose. In other embodiments, the amount of water administered is at least about 200 mL per gram of crosslinked carboxymethylcellulose. In certain embodiments, the amount of water administered is from about 125 mL to about 500 mL or from about 125 mL to about 600 mL. In certain embodiments, the amount of water administered is from 150 mL to 575 mL, from 150 mL to 475 mL, from 200 mL to 550 mL, from 200 mL to 450 mL, from 250 mL to 500 mL or from 200 mL to 400 mL.

The water administered in step (b) can be flat or carbonated water, or in the form of a beverage. Preferably, non-carbonated water is administered. In embodiments in which the water is administered as a beverage, the beverage preferably has pH of about 3 or higher, and more preferably a neutral pH, i.e., a pH between 6 and 8, for example, a pH of about 6.5 to about 7.5, or about 7. Preferably, the beverage has an energy content in the volume administered of 100 kilocalories or less or 50 kilocalories or less. Preferably, the beverage is sugar free. In a preferred embodiment, the water is administered as drinking water, such as tap water, spring water, or purified water.

The subject to be treated is a human or a nonhuman, such as a nonhuman mammal. Suitable nonhuman mammals include domesticated mammals, such as pets, including dogs and cats. Preferably, the subject is a human. The subject can be male or female. The human subject can be of any age, for example, a child, adolescent or adult, but is preferably at least 10 or at least 12 years of age. In one embodiment, the subject is at least 18 years old. When the subject is a child, the dose of crosslinked carboxymethylcellulose is preferably decreased in proportion with the subject's weight.

The subject can be, for example, a human subject for whom weight loss will bring health benefits, such as human who is overweight, with a body mass index of 25 to 29.9, or obese, with a body mass index of 30 or higher. The subject can also be a human of normal weight, with a body mass index of 18.5 to 24.9, but at risk of unhealthy weight increase. A human subject can also have one or more other conditions or comorbidities, such as prediabetes, diabetes or heart disease, in addition to being overweight or obese. For example, the subject can have one or more of the following: hypertension, such as blood pressure of 140/90 mm Hg or higher; high LDL cholesterol; low HDL cholesterol, for example less than 35 mg/dL; high triglycerides, for example higher than 250 mg/dL; high fasting blood glucose, for example, a baseline level of ≥100 mg/dl; a family history of premature heart disease; physical inactivity; and cigarette smoking In one embodiment, the human subject is prediabetic, as determined by one or more of fasting blood glucose level, A1C level and oral glucose tolerance test, according to the criteria established by the American Diabetes Association (*Diabetes Care* 2004, 27:S15-35). For example, a prediabetic subject can have a fasting blood glucose level of 100 mg/dL to 125.9 mg/dL, an A1C level of 5.7 to 6.4% and/or an oral glucose tolerance test result of 140 to 199 mg/dL. Preferably, the prediabetic patient has a baseline fasting blood glucose level of 100 mg/dL to 125.9 mg/dL.

In another embodiment, the human subject is diabetic, as determined by one or more of fasting blood glucose level, A1C level and oral glucose tolerance test. For example, a diabetic subject can have a fasting blood glucose level of 126 mg/dL or higher, an A1C level of 6.5% or higher and/or an oral glucose tolerance test result of 200 mg/dL or higher. Preferably, the diabetic patient has a fasting blood glucose level of 126 mg/dL or higher.

In another embodiment, the subject has metabolic syndrome, as diagnosed using the criteria set forth by the American Heart Association in 2004 (Grundy SM, et al., Circulation. 2004; 109:433-438). According to these guidelines, a subject is diagnosed with metabolic syndrome if at least three of the following five conditions are present: (1) elevated waist circumference (men: >40 inches; women: >35 inches); (2) elevated triglycerides (150 mg/dL or higher); (3) reduced HDL cholesterol (men: less than 40 mg/dL; women: less than 50 mg/dL); (4) elevated blood pressure (130/85 mm Hg or higher) or use of medication for hypertension; (5) fasting blood glucose ≥100 mg/dL or use of medication for hyperglycemia.

In another embodiment, the human subject has an elevated baseline fasting blood glucose level, for example, of about 90 mg/dL or higher or about 93 or 95 mg/dL or higher. Subjects with fasting blood glucose levels in this range include those with fasting blood glucose levels at the high end of the normal range (90 to under 100 mg/dL), prediabetics (blood glucose levels of 100-125.9 mg/dL) and diabetics (blood glucose levels of 126 mg/dL or higher).

It is to be understood that the measurements described above are baseline measurements, that is, the values of the disclosed physiological parameters prior to initiating a method of treatment as described herein. More preferably, such measurements are made in the absence of therapy intended to lower fasting blood glucose levels. Preferably, one or more of these values are determined within about a year of the beginning of treatment according to the invention, more preferably within about six months, even more preferably within about three months and most preferably within about one month.

In another embodiment, the invention provides a method of inducing weight loss in a subject, such as a human subject as described above, wherein the subject has elevated blood glucose at baseline, is prediabetic or is diabetic. The method comprises the step of orally administering to the subject an effective amount of a gelling agent. Preferably the subject is a human having a baseline fasting blood glucose level of about 90 mg/dL or higher or about 93 or 95 mg/dL or higher. In certain embodiments, the subject has a baseline fasting blood glucose level of 100 to 125.9 mg/dL or greater than 126 mg/dL.

In one embodiment, the method comprises orally administering to the subject an effective amount of a gelling agent prior to or concurrently with a meal.

Suitable gelling agents for use in this method include, but are not limited to, fibers, such as dietary fibers, and hydrogels, including both chemically and physically crosslinked absorbent polymers. Particularly suitable hydrogels include superabsorbent polymers. Among these, superabsorbants which are produced using food grade polymers are preferred. For example, suitable gelling agents include polysaccharides and synthetic polymers. Examples of suitable polysaccahrides include glucans, including alpha-glucans, such as starch, dextran, pullulan, and glycogen; beta-glucans, such as cellulose or cellulose derivatives, such as carboxymethylcellulose, hydroxyethylcellulose and methylcellulose, chrysolaminarin, curdlan, laminarin, lentinan, lichenin, pleuran, and zymosan; hemicelluloses, such as glucomannan, arabinoxylan, xylan, glucuronoxylan, and xyloglucan; galactomannans, such as guar gum, fenugreek gum, tara gum, and locust bean gum; pectins; fructans, such as inulin and levan; seaweed gums, such as alginates, algal polysaccharides, agar, and carrageenan; chitin; chitosan; glycosaminoglycans, such as hyaluronic acid, heparin, heparan sulfate, chondroitin sulfate, dermatan sulfate, and keratan sulfate. Each of the foregoing polysaccharides is optionally physically or chemically crosslinked. In one embodiment, the gelling agent is not crosslinked carboxymethylcellulose. In another embodiment, the gelling agent is not citric acid crosslinked carboxymethylcellulose.

Examples of suitable synthetic polymers include poly (ethylene glycol) based polymers; acrylates and acrylate copolymers, such as polyacrylate/polyalcohol copolymers, polyacrylate/polyacrylamide copolymers, crosslinked sodium polyacrylate; polyalcohol polymers, and combinations thereof; polyacrylamide and acrylamide-based products; combinations of gums, such as polyisobutylene, styrene butadiene rubber, and similar with hydrophilic polymers; absorbent polypeptides, such as synthetic proteins generated starting directly from a small number (2 or 3) of amino acids; polyvinyl and polyallyl-alcohol systems, such as polyvinylacetate/vinylalcohol copolymers, crosslinked polyvinyl pyrrolidone; polyamines, such as polyallyl amine, cross-linked with any bifunctional reagent with a double bond, such as a polyolefin; absorbent dendrimers; and poly (lactic acid), polyhydroxyalkanoates, polyvinyl acetatephthalate and copolymers and combinations thereof.

Without being bound by theory, it is believed that such gelling agents retard and/or reduce the uptake of glucose from food. Depending on its structure and degree of swelling in the gastrointestinal tract, the gelling agent is believed to form a diffusion barrier and/or to partially delay the absorption of glucose. For these reasons, it is believed that the hydration kinetics and extent of the gel in the different sections of the gastrointestinal tract play a fundamental role in retarding glucose absorption. Thus, the faster the hydration kinetics and the greater the extent of the gel, the more effective the gel will be. A mild retardation effect is expected for loose fibers and those able to hydrate with slow kinetics and to only a limited extent. Greater glucose retardation is expected to be achieved by crosslinked hydrogels, particularly by superabsorbent hydrogels.

The methods of inducing weight loss and treating overweight or obesity of the invention, as described above, are particularly useful in subjects having elevated baseline fasting blood glucose, including prediabetic and diabetic subjects. Thus, a subject's fasting blood glucose level indicates whether the subject is likely to particularly benefit from treatment. In one embodiment, the methods for inducing weight loss of the invention further include the step of identifying a subject to receive the treatment according to one of the disclosed methods, prior to the initiation of treatment. This step comprises determining the baseline fasting blood glucose level of the subject, wherein if the subject has an elevated baseline fasting blood glucose level, as defined above, the subject is treated according to a method of inducing weight loss as described herein.

In another embodiment, the invention provides a method of modifying the macronutrient preferences of a subject with elevated fasting blood glucose at baseline. The method comprises regulating the blood glucose level of the subject. In one embodiment, the method comprises administering to the subject an effective amount of an agent which improves glycemic control. The agent can be crosslinked carboxymethylcellulose or a gelling agent as described above, which is orally administered. The term "macronutrients" as used herein, refers to carbohydrates, fats and protein. In a preferred embodiment, the method results in reduced consumption of carbohydrates and, preferably, increased consumption of protein. Such a method results in further enhanced glycemic control and increased weight loss.

Treatment of Diabetes and Improvement of Glycemic Control

In another embodiment, the invention provides a method of treating diabetes or improving glycemic control in a subject in need thereof. The method comprises the step of orally administering to the subject from about 0.7 to about 4 g of crosslinked carboxymethylcellulose per administration. In one embodiment, the method is conducted prior to or concurrently with at least one meal per day. In certain embodiments, the method is conducted prior to or with two meals per day. In certain embodiments, the method is conducted prior to or with three meals per day. In certain embodiments, the subject is directed to eat four or more meals per day, and the method is conducted prior to or with at least one meal and up to every meal per day.

In one embodiment, the amount of crosslinked carboxymethylcellulose administered with or prior to the meal is from about 1.0 g to about 3.5 g. In certain embodiments, the amount of crosslinked carboxymethylcellulose administered with or prior to the meal is from 1.1 to about 3.5 g or about 1.5 g to 3.5 g. In certain embodiments, the amount of crosslinked carboxymethylcellulose administered with or prior to the meal is from 1.75 g to 3.25 g, or from 2.0 g to 3.0 g. In certain embodiments, the amount of crosslinked carboxymethylcellulose administered with or prior to the meal is from 2.15 to 2.35 g. In certain embodiments, the amount of crosslinked carboxymethylcellulose administered with or prior to the meal is about 2.25 g.

In one embodiment, the method is conducted with or prior to one meal per day and the daily amount of crosslinked carboxymethylcellulose administered is from about 1.1 g to about 2.25 g. In one embodiment, the method is conducted with or prior to two meals per day and the daily amount of crosslinked carboxymethylcellulose administered is from about 1.1 g to about 4.5 g, preferably from about 2.2 g to 4.5 g. In one embodiment, the method is conducted prior to three meals per day and the daily amount of crosslinked carboxymethylcellulose administered is from about 1.65 g to about 6.75 g, preferably from about 3.3 g to about 6.75 g. In one embodiment, the method is conducted with or prior to four meals per day and the daily amount of crosslinked carboxymethylcellulose administered is from about 2.2 g to about 6 g, preferably from about 4.4 g to about 6 g.

The crosslinked carboxymethylcellulose can be administered with or without water. Typically, the crosslinked carboxymethylcellulose is administered with at least sufficient water to facilitate swallowing of the crosslinked carboxymethylcellulose. In certain embodiments, the crosslinked carboxymethylcellulose is administered with a volume of water in excess of the amount required for swallowing the crosslinked carboxymethylcellulose. In one embodiment, about 50 mL to about 250 mL of water per gram of crosslinked carboxymethylcellulose is administered. In certain embodiments the amount of water administered is from about 125 mL to about 225 mL per gram of crosslinked carboxymethylcellulose. In other embodiments, the amount of water administered is from about 150 mL to about 200 mL per gram of crosslinked carboxymethylcellulose. In certain embodiments, the amount of water administered is from about 250 mL to about 750 mL. In certain embodiments, the amount of water administered is from 300 mL to 650 mL, from 350 mL to 600 mL or from 500 mL to 550 mL. In certain embodiments, the amount of water administered is about 500 mL.

The water administered can be flat or carbonated water, or in the form of a beverage. Preferably, non-carbonated water is administered. In embodiments in which the water is administered as a beverage, the beverage preferably has a pH of 3 or greater, more preferably a neutral pH, i.e., a pH between 6 and 8, for example, a pH of about 6.5 to about 7.5, or about 7. Preferably, the beverage has an energy content in the volume administered of 100 kilocalories or less or 50 kilocalories or less. Preferably, the beverage is sugar free. In a preferred embodiment, the water is administered as drinking water, for example, tap water, spring water or purified water.

In one embodiment, the crosslinked carboxymethylcellulose is administered from the beginning of the meal up to 1 hour prior to the meal, from 0 to 40 minutes, from 5 to 35 minutes prior to the meal or from 10 to 30 minutes prior to the meal. In another embodiment, the crosslinked carboxymethylcellulose is administered immediately before the meal or with the meal.

In an embodiment, the method is conducted daily up to one week, up to four weeks, up to eight weeks, up to twelve weeks, up to sixteen weeks, up to twenty weeks, up to twenty-four weeks, up to 36 weeks, or up to one year or longer. In some embodiments, the method is conducted chronically, i.e., for a period of greater than one year or for an indefinite period. In some embodiments, the method is conducted daily for a first period of time, stopped for a second period and then conducted for a third period of time. This alternation of treatment periods and nontreatment periods can be conducted over multiple cycles or continued indefinitely. The treatment period selected will depend on the needs of the subject, for example, as determined by the treating physician.

The subject to be treated is a human or a nonhuman, such as a nonhuman mammal. Suitable nonhuman mammals include domesticated mammals, such as pets, including dogs and cats. Preferably, the subject is a human. The subject can be male or female. The human subject can be any age, for example, a child, an adolescent or an adult. In one embodiment, the subject is at least 10 or at least 12 years of age. In another embodiment, the subject is at least 18 years of age. The subject can be, for example, a human subject suffering from diabetes or at risk of developing diabetes, for example a subject diagnosed with prediabetes. When the subject is a child, the dose of crosslinked carboxymethylcellulose is preferably decreased in proportion with the subject's size.

In one embodiment, the human subject is prediabetic, as described above. In another embodiment, the subject is diabetic, as described above.

In another embodiment, the subject has an elevated fasting blood glucose level, for example, a fasting blood glucose level of about 90 mg/dL or higher or about 93 or 95 mg/dL or higher. Subjects with fasting blood glucose levels in this range include those with fasting blood glucose levels in the high end of normal (90 to under 100 mg/dL), prediabetics (fasting blood glucose levels of 100 to 125.9 mg/dL) and diabetics (fasting blood glucose levels of 126 mg/dL or higher).

The subject can be normal weight, overweight or obese. In certain embodiments, the improvement in glycemic control and/or the symptoms of diabetes is accompanied by weight loss, for example, of about 5% of baseline body weight or more. In other embodiments, the improvement in glycemic control and/or the symptoms of diabetes is accompanied by weight loss, for example, of less than about 5% of baseline body weight. In still other embodiments, the improvement in glycemic control and/or the symptoms of diabetes is accompanied by no or insignificant weight loss.

It is to be understood that the measurements described above are baseline measurements, that is the values of the disclosed physiological parameters prior to the commencement of the method of treatment described herein. Preferably, one or more of the disclosed parameters are determined prior to the commencement of treatment with the crosslinked carboxymethylcellulose. More preferably, one or more of these values are determined within six months of the beginning of treatment, more preferably within three months and most preferably within about one month.

Crosslinked Carboxymethylcellulose

Carboxymethylcellulose can be chemically crosslinked using any method which results in the formation of a biocompatible product having sufficient absorption and mechanical properties for use in the present method. For example, the carboxymethylcellulose can be crosslinked with a multifunctional cross linking agent or with radiation. In another embodiment, the carboxymethylcellulose is crosslinked by formation of ester linkages between polysaccharide strands, for example, by heating at an acidic pH or by use of a carboxyl activating agent such as a carbodiimide.

In the methods of the invention, the crosslinked carboxymethylcellulose is administered in a substantially dehydrated state, that is, consisting of less than about 25% water by weight, preferably less that about 20%, 15%, 10% or 7% water by weight.

The crosslinked carboxymethylcellulose is preferably a glassy amorphous material when in a substantially dry or xerogel form. In an embodiment, the polymer hydrogels of the invention have a bulk density or a tapped density of higher than about 0.3 g/cm$^3$. In preferred embodiments, the bulk density or tapped density is higher than about 0.5 g/cm$^3$ or from about 0.55 to about 0.8 g/cm$^3$ when determined as described in US Pharmacopeia <616>, incorporated herein by reference. In a preferred embodiment, the bulk or tapped density is about 0.6 g/cm$^3$ or higher, for example, from about 0.6 g/cm$^3$ to about 0.8 g/cm$^3$.

Preferably the crosslinked carboxymethylcellulose has a water content of less than about 10% by weight, a tapped density of at least about 0.6 g/cm$^3$, an elastic modulus of at least about 350 Pa, and/or a media uptake ratio of at least about 50 in a 1:8 (vol/vol) mixture of simulated gastric fluid ("SGF", USP 33-28F) and water. More preferably the crosslinked carboxymethylcellulose has each of the foregoing properties.

Determination of tapped density, media uptake ratio (MUR) and elastic modulus can be conducted as described in Example 1.

In a particularly preferred embodiment, the crosslinked carboxymethylcellulose is provided as particles which are substantially in the size range of 10 μm to 1000 μm. In one embodiment, at least about 95% of the crosslinked carboxymethylcellulose by weight consists of particles in the size range of 100 μm to 1000 μm or 400 μm to 800 μm.

Preferably, the carboxymethylcellulose is crosslinked starting from a salt, for example, the sodium salt.

In one embodiment, the carboxymethylcellulose is crosslinked with a polycarboxylic acid. Preferably, the carboxymethylcellulose is crosslinked with citric acid. Suitable methods for crosslinking carboxymethylcellulose with citric acid are described in US 2013/0089737, WO 2010/059725, WO 2009/022358 and WO 2009/021701, each of which is incorporated herein by reference in its entirety. In one embodiment, the carboxymethylcellulose is crosslinked via a method comprising the steps of (a) producing an aqueous solution or carboxymethylcellulose and citric acid; (b) removing water from the solution, for example by evaporation, to produce a solid residue and (c) heat treating the solid residue to form a crosslinked carboxymethylcellulose.

In preferred embodiments, the crosslinked carboxymethylcellulose is prepared by a method comprising the following steps: Step 1, carboxymethylcellulose sodium salt and citric acid are dissolved in purified water to produce a solution essentially consisting of about 5% to about 7%, preferably about 6%, carboxymethylcellulose by weight relative to the weight of water, and citric acid in an amount of about 0.15% to about 0.35% or about 0.15% to about 0.30% by weight relative to the weight of carboxymethylcellulose; Step 2, maintaining the solution at a temperature from about 40° C. to about 70° C. or 40° C. to about 80° C., preferably about 70° C., to evaporate the water and form a solid carboxymethylcellulose/citric acid composite; Step 3, grinding the composite to form composite particles; and Step 4, maintaining the composite particles at a temperature from about 80° C. to about 150° C. or about 100° C. to about 150° C., preferably, about 120° C., for a period of time sufficient to achieve the desired degree of cross-linking and form the polymer hydrogel. The method can optionally further include Step 5, washing the polymer hydrogel with purified water; and Step 6, drying the purified polymer hydrogel at elevated temperature. A process for the large scale production of a suitable crosslinked carboxymethylcellulose is described in Example 1.

The crosslinked carboxymethylcellulose is preferably crosslinked with citric acid and has a crosslinked and singly bonded citric acid to carboxymethylcellulose ratio of 0.05 to 1% wt/wt and more preferably a ratio of 0.1 to 0.4% wt/wt. Still more preferably, the crosslinked and singly bonded citric acid to carboxymethylcellulose ratio is 0.225 to 0.375% wt/wt.

The crosslinked carboxymethylcellulose preferably has a degree of cross-linking from about $2.5 \times 10^{-5}$ mol/cm$^3$ to about $5 \times 10^{-5}$ mol/cm$^3$, more preferably from about $4 \times 10^{-5}$ mol/cm$^3$ to about $5 \times 10^{-5}$ mol/cm$^3$.

Formulations

The crosslinked carboxymethylcellulose can be administered to the subject in the form of a tablet, a capsule, a powder, a suspension, a sachet or any other formulation suitable for oral administration. The tablet or capsule can further include one or more additional agents, such as a pH modifying agent, and/or a pharmaceutically acceptable carrier or excipient. In a preferred embodiment, the crosslinked carboxymethylcellulose is loaded into soft or hard gelatin capsules in the substantial absence of other excipients. Any size capsules can be used; the number of capsules administered per dose will depend on the capacity of the selected capsule. In one embodiment, the crosslinked carboxymethylcellulose is loaded into size 00el soft gelatin capsules in an amount of 0.50 to 1.00 g per capsule, preferably 0.60 to 0.90 g, more preferably 0.70 to 0.80 g and most preferably about 0.75 g per capsule.

EXAMPLES

The invention now being generally described, it will be more readily understood by the following examples, which are included merely for purposes of illustration of certain aspects and embodiments of the present invention and are not intended to limit the invention.

Example 1

Production of Crosslinked Carboxymethylcellulose

Citric acid crosslinked carboxymethylcellulose ("CMC/CA") was prepared as described in US Patent Application Publication 2013/0089737, incorporated herein by reference in its entirety. Specifically, sodium carboxymethylcellulose (6% wt/wt water), citric acid (0.3% wt/wt sodium carboxymethylcellulose) and water was mixed at room temperature and pressure in a low shear mixing vessel until a homogeneous solution is formed. The solution was transferred to trays so as to maintain a solution depth of about 30 mm. The trays were placed in an atmospheric forced air oven and dried for 16 to 24 hours at 85° C. The temperature was then lowered to 50° C. until drying was complete. The total drying time was about 60 hours. The resulting residue was in the form of a sheet, which was ground using a coarse mill and fine mill and sieved to provide a sample comprising particles of size between 100 and 1600 μm. The particles were placed in a crosslink reactor and maintained at 120° C. and atmospheric pressure for 3 to 10 hours. The resulting hydrogel was transferred to a wash tank and washed at ambient temperature and pressure with an amount of water between 150 and 300 times the polymer weight. The free water was removed from the hydrogel by filtration. The hydrogel was placed on trays at a thickness of about 40 mm. The trays were placed in an atmospheric forced air oven and dried for 24-30 hours at 85° C. The temperature was then lowered to 50° C. until dry. The total drying time was about 60 hours. The dried material was ground into particles using a fine mill and mechanically sieved to obtain particle fractions between 100 and 1000 µm.

Using the general process described above and starting with higher than 4 kg of sodium carboxymethylcellulose, the yield was over 70% of powder with a particle size range between 100 and 1000 µm. The powdered hydrogel product met the product specifications as detailed in the table below.

TABLE 1

Final Product Specifications

| Attribute | Specifications | Method |
|---|---|---|
| Media uptake | Not Less Than 50x reported as g/g | 1 g in 200 mL SGF/water 1:8 for 30 minutes |
| Particle size distribution | At least 95% of particles between 100 and 1000 µm | Estimation by analytical sieving |
| Tapped density | Not Less Than 0.6 g/mL | Bulk density and tapped density of powders. |
| Elastic modulus | Not Less Than 350 Pa | Analysis of swollen particles with parallel plate rheometer |
| Loss on drying | Not More Than 10% | Loss on drying at 100° C. for 20 minutes |

The CMC/CA powder was loaded into gelatin capsules in an amount of 0.75 g per capsule.

The CMC/CA powder was characterized according to the methods below.

Preparation of Simulated Gastric Fluid/Water (1:8)

Reagents used for preparation of SGF/water (1:8) solution are purified water, sodium chloride, 1M hydrochloric acid and pepsin.
1. To a 1 L graduated cylinder pour about 880 ml of water.
2. Place the cylinder on a magnetic stirrer, add a magnetic bar and start stirring.
3. Begin monitoring the pH of the water with a pH meter.
4. Add a sufficient amount of 1M hydrochloric acid to bring the pH to 2.1±0.1.
5. Add 0.2 g NaCl and 0.32 g pepsin. Leave the solution to stir until complete dissolution.
6. Remove the magnetic bar and the electrode from the cylinder.
7. Add the amount of water required to bring the volume to 900 ml.

Determination of Tapped Density

Equipment and materials:
100 mL glass graduated cylinder,
100 mL glass beaker,
Lab spatula,
Mechanical tapped density tester, Model JV 1000 by Copley Scientific,
Calibrated balance capable of weighing to the nearest 0.1 g.

Procedure:
1. Weigh out 40.0±0.1 grams of test sample. This value is designated M.
2. Introduce the sample into a dry 100 mL glass graduated cylinder.
3. Carefully level the powder without compacting and read the unsettled apparent volume, V0, to the nearest graduated unit.
4. Set the mechanical tapped density tester to tap the cylinder 500 times initially and measure the tapped volume, V500, to the nearest graduated unit.
5. Repeat the tapping 750 times and measure the tapped volume, V750, to the nearest graduated unit.
6. If the difference between the two volumes is less than 2%, V750 is the final tapped volume, Vf, otherwise repeat in increments of 1250 taps, as needed, until the difference between succeeding measurements is less than 2%.

Calculations:
Calculate the Tapped Density, DT, in gram per mL, by the formula:

$$DT=M/Vf$$

where:
M=Weight of sample, in grams, rounded off to the nearest 0.1 g.
Vf=Final volume, in mL.

Determination of Media Uptake Ratio in SGF/Water (1:8)

The media uptake ratio of a crosslinked carboxymethylcellulose in SGF/water (1:8) is determined according to the following protocol.
1. Place a dried fitted glass funnel on a support and pour 40.0±1.0 g of purified water into the funnel.
2. Wait until no droplets are detected in the neck of the funnel (about 5 minutes) and dry the tip of the funnel with an absorbent paper.
3. Place the funnel into an empty and dry glass beaker (beaker #1), place them on a tared scale and record the weight of the empty apparatus ($W_{tare}$).
4. Put a magnetic stir bar in a 100 mL beaker (beaker #2); place beaker #2 on the scale and tare.
5. Add 40.0±1.0 g of SGF/Water (1:8) solution prepared as described above to beaker #2.
6. Place beaker #2 on the magnetic stirrer and stir gently at room temperature.
7. Accurately weigh 0.250±0.005 g of crosslinked carboxymethylcellulose powder using a weighing paper ($W_{in}$).
8. Add the powder to beaker #2 and stir gently for 30±2 min with the magnetic stirrer without generating vortices.
9. Remove the stir bar from the resulting suspension, place the funnel on a support and pour the suspension into the funnel, collecting any remaining material with a spatula.
10. Allow the material to drain for 10±1 min.
11. Place the funnel containing the drained material inside beaker #1 and weigh it ($W'_{fin}$).

The Media Uptake Ratio (MUR) is calculated according to:

$$MUR=(W_{fin}-W_{in})/W_{in}.$$

$W_{fin}$ is the weight of the swollen hydrogel calculated as follows:

$$W_{fin}=W'_{fin}-W_{tare},$$

$W_{in}$ is the weight of the initial dry sample.
The MUR is determined in triplicate for each sample of crosslinked carboxymethylcellulose and the reported MUR is the average of the three determinations.

Determination of Elastic Modulus

The elastic modulus (G') is determined according to the protocol set forth below. The rheometer used is a Rheometer Discovery HR-1 (5332-0277 DHR-1) by TA Instruments or equivalent, equipped with a Peltier Plate; a Lower Flat plate Xhatch, 40 mm diameter; and an Upper Flat plate Xhatch, 40 mm diameter.
1. Put a magnetic stir bar in a 100 mL beaker.
2. Add 40.0±1.0 g of SGF/Water (1:8) solution prepared as described above to the beaker.
3. Place the beaker on the magnetic stirrer and stir gently at room temperature.
4. Accurately weigh 0.250±0.005 g of crosslinked carboxymethylcellulose powder using a weighing paper ($W_{in}$).

5. Add the powder to the beaker and stir gently for 30±2 min with the magnetic stirrer without generating vortices.
6. Remove the stir bar from the resulting suspension, place the funnel on a support and pour the suspension into the funnel, collecting any remaining material with a spatula.
7. Allow the material to drain for 10±1 min.
8. Collect the resulting material.
9. Subject the material to a sweep frequency test with the rheometer and determine the value at an angular frequency of 10 rad/s.

The determination is made in triplicate. The reported G' value is the average of the three determinations.

Example 2

Clinical Study of Crosslinked Carboxymethylcellulose

A clinical study of the CMC/CA formulation described in Example 1 was conducted.

Study design: a 12-week study to determine the effect of repeated administration of CMC/CA on body weight in overweight and obese subjects. The study was conducted at five European sites. One hundred twenty-eight subjects, with a mean BMI of 31.7, were randomized into three arms: CMC/CA 2.25 g, CMC/CA 3.75 g, and placebo. Subjects ingested either CMC/CA or placebo 30 minutes before lunch and dinner with two glasses of water. The placebo capsules contained microcrystalline cellulose, a non-digestible fiber and bulking agent with low water absorption capacity and potential weight-loss properties. All subjects received dietary counseling designed to reduce their calorie intake by 600 kcal/day below their daily requirement. One hundred twenty-five subjects had at least one post-baseline assessment of body weight (intention-to-treat "ITT" population). Forty-two of the ITT subjects were on CMC/CA 2.25 g, 41 on CMC/CA 3.75 g, and 42 on placebo. One hundred ten subjects completed the key visit of the study at Day 87 for the assessment of body weight. One hundred twenty-six subjects provided post-randomization safety data through Day 87. The primary efficacy endpoint of change in body weight from baseline was assessed by analysis of the covariance (ANCOVA) model in the ITT population with baseline weight, gender, and BMI status as covariates (possible predictors of the outcome).

Efficacy Endpoints

Primary: Body weight (Week 13)

Secondary: Body weight responders (5% weight loss) (Week 13); waist circumference (Week 13); fat mass and bone-free fat-free mass (DEXA) (Week 13); appetite (visual analogue scales) (Week 12); food intake (24-h dietary recall) (Week 12).

Study Duration 12-week treatment period plus 10-day post-treatment follow-up period.

TABLE 2

Sample Size & Power

| Parameter | Value |
| --- | --- |
| Power | 90% |
| Significance level | 0.025 |
| One-versus two-sided | One-sided |

TABLE 2-continued

Sample Size & Power

| Parameter | Value |
| --- | --- |
| Placebo-adjusted weight loss | 2% |
| Standard deviation | 2.5% |

TABLE 3

Characteristics of Intention to Treat Population

| Parameter | Placebo (n = 42) | CMC/CA 2.25 g (n = 42) | CMC/CA 3.75 g (n = 41) | All Arms (n = 125) |
| --- | --- | --- | --- | --- |
| Male (n) | 13 (31%) | 13 (31%) | 14 (34%) | 40 (32%) |
| Female (n) | 29 (69%) | 29 (69%) | 27 (66%) | 85 (68%) |
| Age (years) | 44.0 ± 11.7 | 42.4 ± 12.3 | 46.1 ± 11.2 | 44.2 ± 11.7 |
| BMI | 32.0 ± 2.3 | 31.2 ± 2.3 | 31.8 ± 2.5 | 31.7 ± 2.4 |
| Overweight (n) | 12 (29%) | 13 (31%) | 12 (29%) | 37 (30%) |
| Obese (n) | 30 (71%) | 29 (69%) | 29 (71%) | 88 (70%) |
| Glucose (mmol/L) | 5.31 ± 0.58 | 5.18 ± 0.54 | 5.20 ± 0.50 | 5.23 ± 0.54 |

Results

The results of the study are set forth in Table 4, below, and in FIGS. 1 to 4.

TABLE 4

Intention to Treat Population

| Type of Response | Placebo (n = 42) | CMC/CA 2.25 g (n = 42) | CMC/CA: 3.75 g (n = 41) |
| --- | --- | --- | --- |
| Weight gain | 7 (17%) | 3 (7%) | 9 (22%) |
| 0 < Weight loss < 5% | 18 (43%) | 21 (50%) | 13 (32%) |
| Weight loss ≥5% | 17 (40%) | 18 (43%) | 19 (46%) |
| Weight loss ≥10% | 5 (12%) | 11 (26%) | 5 (12%) |

The results show that subjects in the low dose CMC/CA arm had a lower rate of weight gain and a higher rate of weight loss of 10% or more compared to the placebo and high dose CMC/CA groups. As shown in FIG. 1 and Table 5 below, repeated administration of low dose CMC/CA over 12 weeks to overweight and obese subjects resulted in significantly decreased body weight compared to placebo without reaching a plateau. Weight loss in this group was also significantly greater than in the high dose CMC/CA group. Weight loss was greater in the low dose CMC/CA arm for subjects with higher than median fasting blood glucose (>5.15 mmol/L (>93 mg/dL)) at baseline, especially in those with impaired fasting blood glucose (≥5.6 mmol/L (≥100 mg/dL)).

Figure 6:
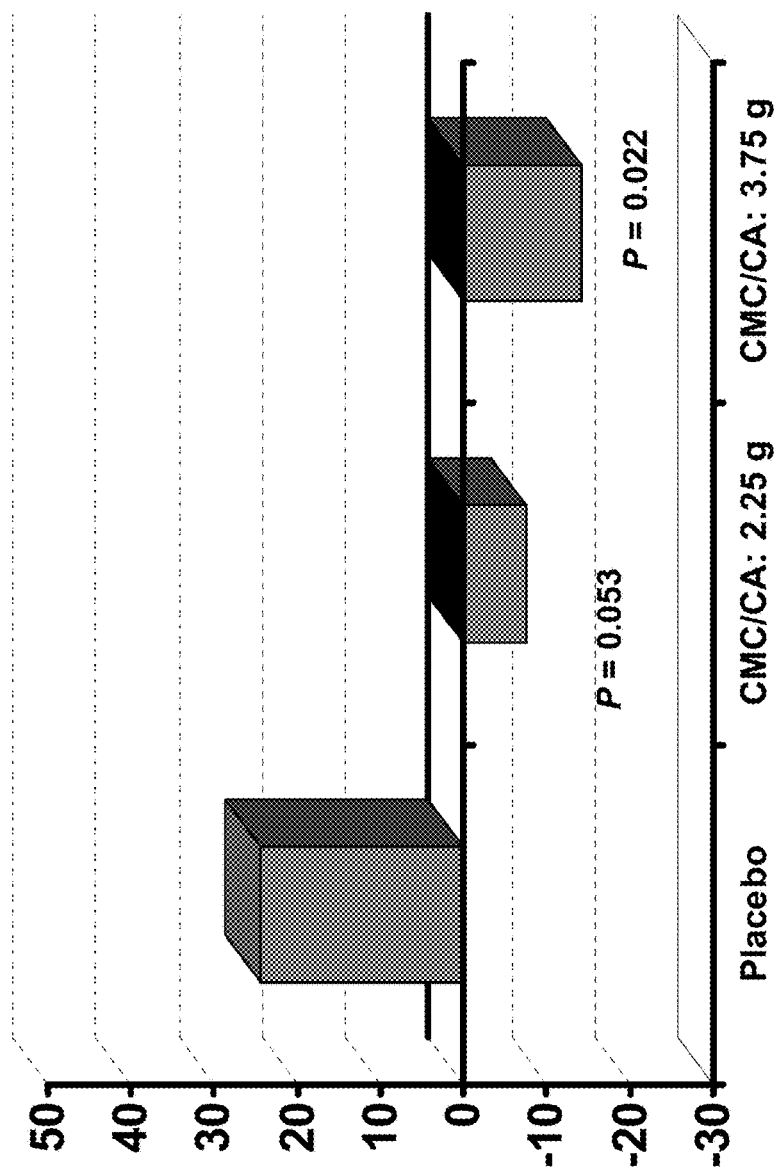
FIG. 6 is a graph showing change in serum insulin concentration (% change from baseline) in the placebo (n=42), CMC/CA 2.25 g (n=41) and CMC/CA 3.75 g (n=37) groups over the course of the study described in Example 2.
Figure 7:
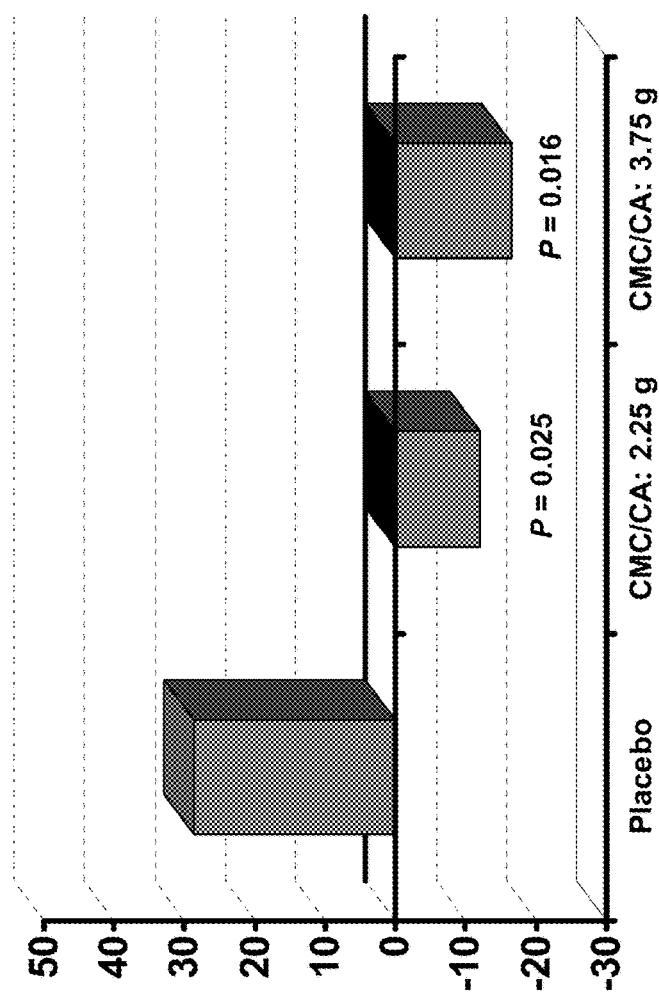
FIG. 7 is a graph showing the change in insulin resistance (% change from baseline) by homeostatic model assessment in the placebo (n=42), CMC/CA 2.25 g (n=41) and CMC/CA 3.75 g (n=37) groups over the course of the study described in Example 2.
Figure 8:
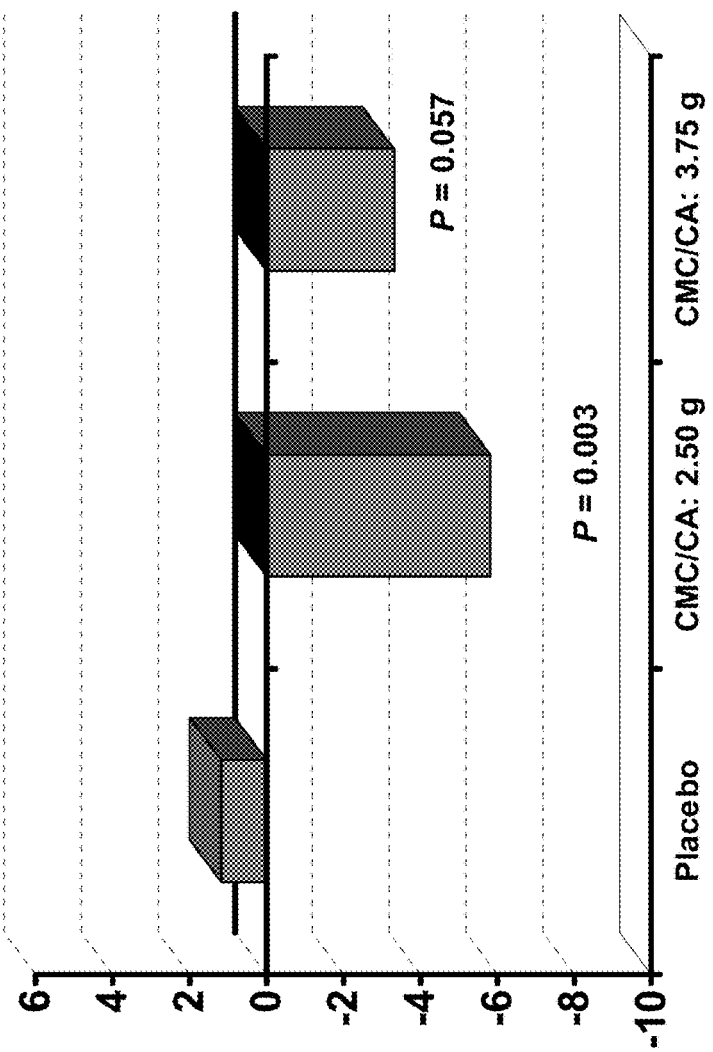
FIG. 8 is a graph showing the change in fasting blood glucose (% change from baseline) in the placebo (n=42), CMC/CA 2.25 g (n=41) and CMC/CA 3.75 g (n=39) groups over the course of the study described in Example 2.

Body weight decreased significantly by Day 87 in patients on CMC/CA 2.25 g with a placebo-adjusted weight loss of 2.0% and a total body weight loss of 6.1%, while patients in the CMC/CA 3.75 g arm had a total body weight loss of 4.5% (0.4% placebo-adjusted). It is believed that the lower observed efficacy in the CMC/CA 3.75 g arm compared with the CMC/CA 2.25 g arm can be explained by two factors: lower tolerability and insufficient water intake. Patients in the CMC/CA 3.75 g arm reported GI adverse events at a higher rate (76%) than patients in the CMC/CA 2.25 g arm (60%). In addition, 10 patients, or 24%, from the CMC/CA 3.75 g arm dropped out of the study, with 8 of the dropouts reporting GI AEs, as compared with two patients, or 5%, who dropped out from CMC/CA 2.25 g arm, with no GI AEs. When looking specifically at the nonresponders in each arm, in the CMC/CA 3.75 g arm, a statistically significant increase in serum albumin (a surrogate marker for hemoconcentration, which is the decrease of the fluid content of the blood) of 1.8 g/L (p=0.01) is observed, compared with a decrease of 0.3 g/L in the placebo arm and a decrease of 0.7 g/L in the CMC/CA 2.25 g arm. To maintain a blinded study, the same volume of water was required at capsule administration for all arms in the trial. The assumption was that the volume of water administered with the capsules, in addition to gastric fluids and liquids consumed during the meal, would be sufficient to hydrate both the CMC/CA 2.25 g dose and the CMC/CA 3.75 g dose. Based on the hemoconcentration observed in the nonresponders in the CMC/CA 3.75 g arm, it is believed that these patients did not drink enough liquids during the meal, resulting in the overall lower weight loss in this arm. However, although the higher dose of 3.75 g was less effective for weight loss possibly due to the reasons mentioned here, it was at least the same or even more effective for glycemic control.

conversion of impaired fasting blood glucose status to normal fasting blood glucose status (% of subjects) in the intent to treat population. FIG. 6 shows the change in serum insulin levels (% change from baseline) over the course of the study. A significant decrease in serum insulin relative to placebo was observed in the CMC/CA 3.75 g arm. FIG. 7 shows the decrease of insulin resistance in the intent to treat population, as determined by homeostatic model assessment. A significant decrease in insulin resistance compared to placebo was observed in both CMC/CA arms. FIG. 8 shows the change in glucose levels (% change from baseline) over the course of the study. The results show that treatment with CMC/CA 2.25 g significantly improved glycemic control.

Table 6 shows the baseline glycemic control parameters in the intent to treat population. The population included subjects with normal and impaired fasting blood glucose levels but no diabetic subjects. Table 7 shows the glucose status in the intent to treat population.

TABLE 6

| Parameter | Placebo (n = 42) | CMC/CA 2.25 g (n = 42) | CMC/CA 3.75 g (n = 41) | All Arms (n = 125) |
|---|---|---|---|---|
| Insulin (mU/l) | 7.7 ± 4.1 | 6.7 ± 3.1 | 8.2 ± 3.9 | 7.5 ± 3.7 |
| HOMA-IR | 1.9 ± 1.1 | 1.6 ± 0.7 | 1.9 ± 1.0 | 1.8 ± 1.0 |
| Glucose (mmol/L) | 5.31 ± 0.58 | 5.18 ± 0.54 | 5.20 ± 0.50 | 5.23 ± 0.54 |
| High glucose* (n) | 22 | 21 | 19 | 62 |
| Low glucose** (n) | 20 | 21 | 22 | 63 |
| HbA1c (mmol/mol) | 42 ± 5 | 40 ± 4 | 42 ± 4 | 41 ± 4 |

*>93 mg/dL;
**≤93 mg/dL

TABLE 5

| Mean % Weight Change | Treatment Arm | | Placebo adjusted |
|---|---|---|---|
| | Placebo | CMC/CA 2.25 g | |
| Intent to treat population | −4.1% (n = 42) | −6.1% (n = 42) | −2.0% (p = 0.026) |
| Baseline fasting blood glucose >93 mg/dL | −4.4% (n = 22) | −8.2% (n = 21) | −3.8% (p = 0.006) |
| Baseline fasting blood glucose ≥100 mg/dL | −5.6% (n = 11) | −10.9% (n = 9) | −5.3% (p = 0.019) |

Figure 2A:
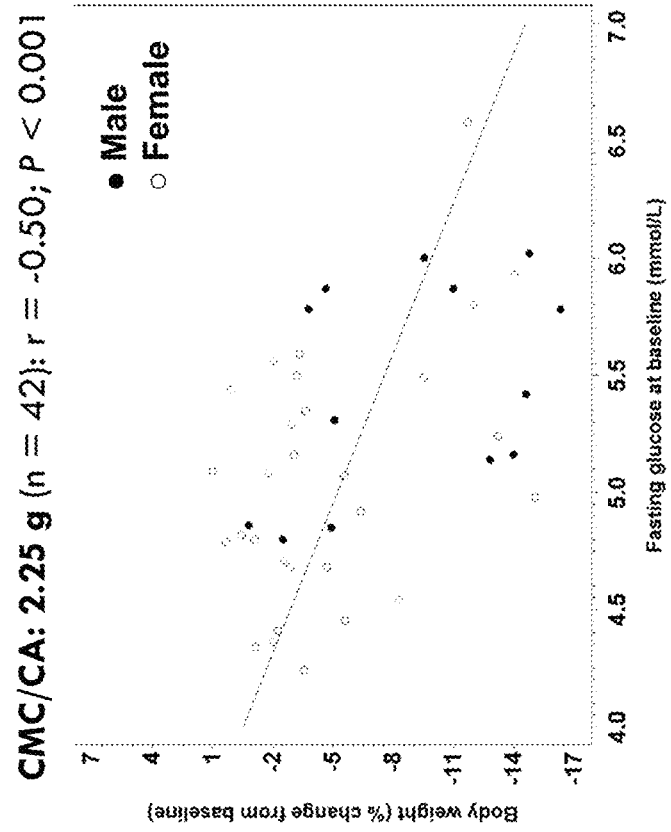
FIG. 2A is a graph showing the relation between fasting blood glucose at baseline and body weight change over the course of the study described in Example 2 for the CMC/CA 2.25 g arm.
Figure 2B:
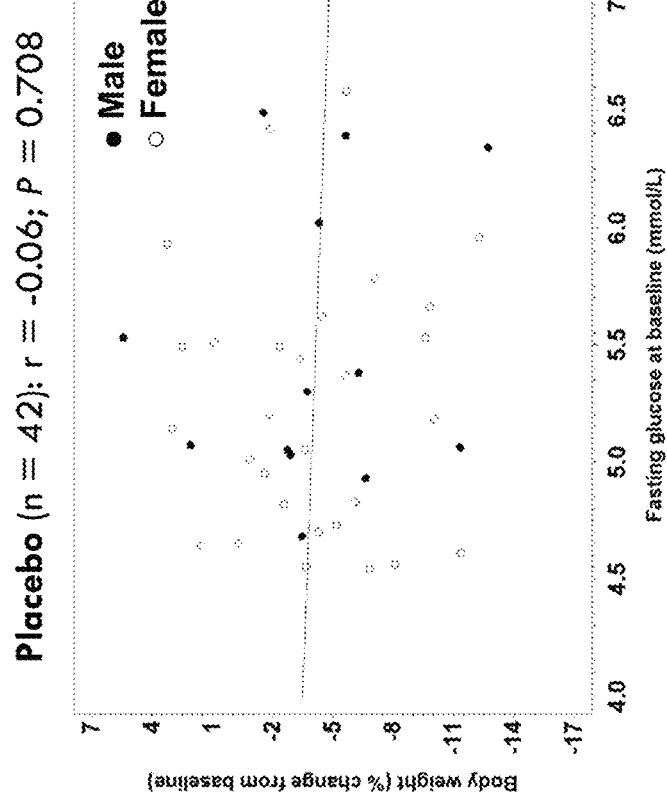
FIG. 2B is a graph showing the relation between fasting blood glucose at baseline and body weight change over the course of the study described in Example 2 for the placebo group.

As shown in FIGS. 2A and 2B, there was a significant inverse correlation between fasting blood glucose level at baseline and change in body weight in CMC/CA 2.25 g arm (r=−0.50; P<0.001), contrasting with a lack of correlation in the placebo arm (r=−0.06; P=0.708).

Figure 3:
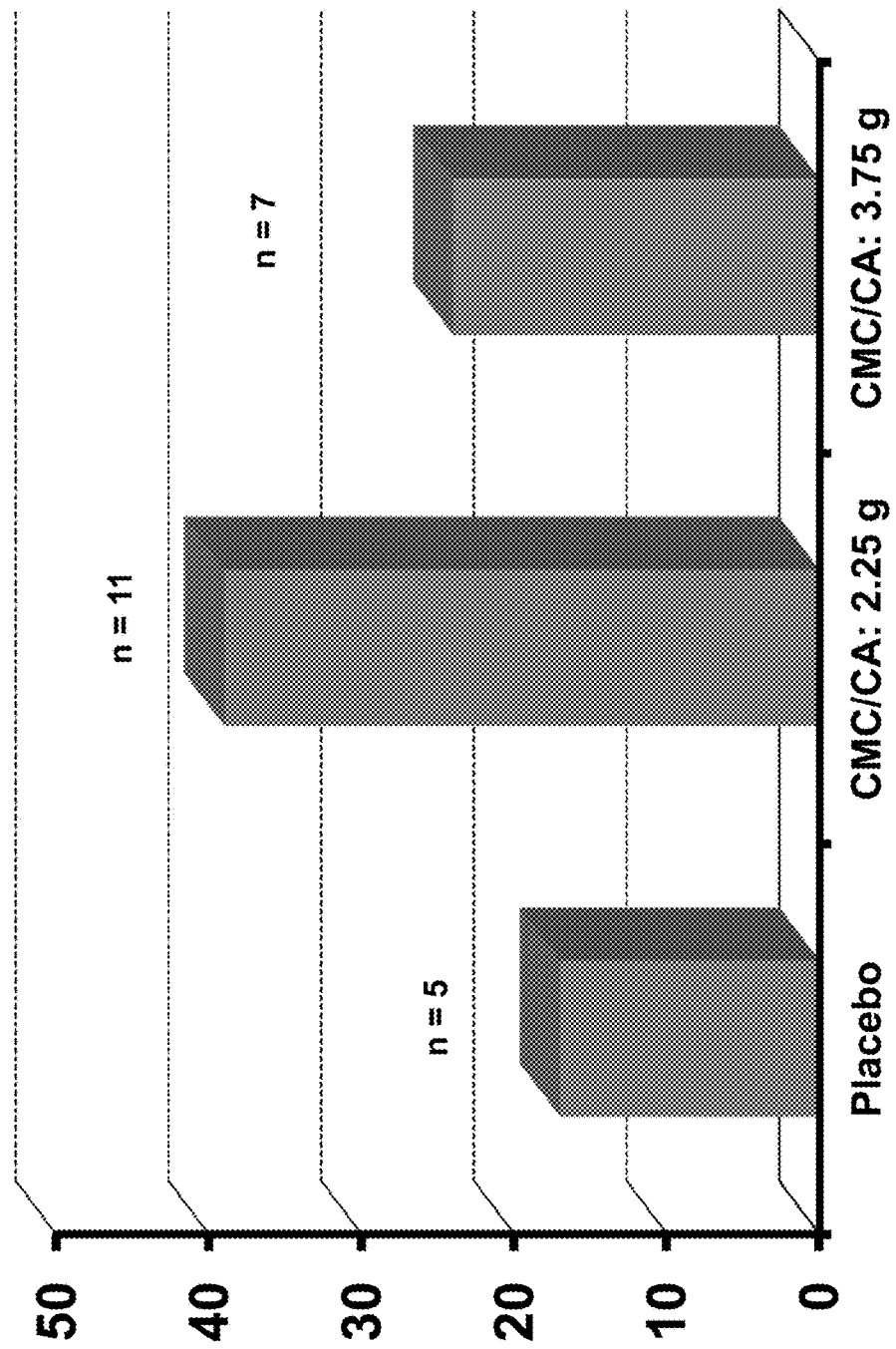
FIG. 3 is a graph showing conversion of obese status to overweight status (% of subjects) in the placebo (n=30), CMC/CA 2.25 g (n=28) and CMC/CA 3.75 g (n=29) groups over the course of the study described in Example 2.
Figure 4:
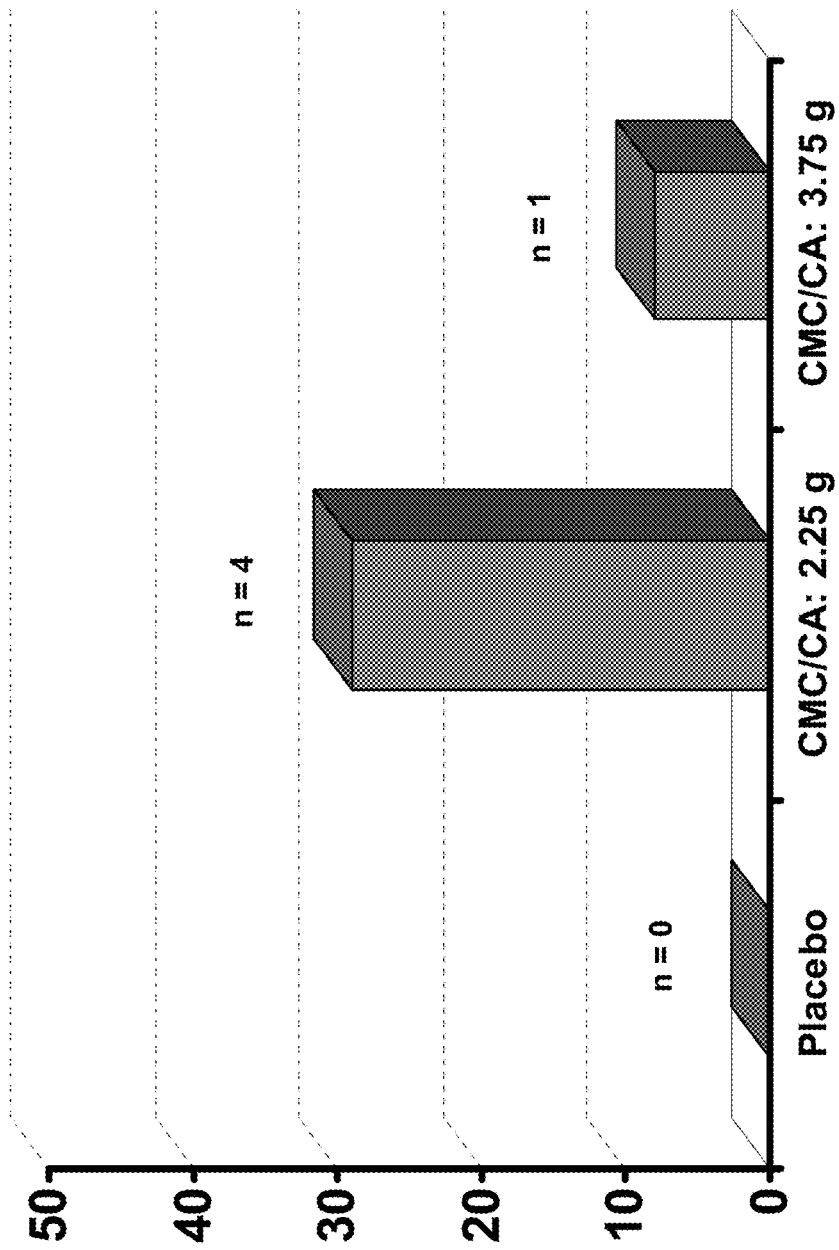
FIG. 4 is a graph showing conversion of overweight status to normal weight status (% of subjects) in the placebo (n=12), CMC/CA 2.25 g (n=14) and CMC/CA 3.75 g (n=12) groups over the course of the study described in Example 2.

FIGS. 3 and 4 show respectively conversion of obese status to overweight status (% of subjects) and conversion of overweight status to normal weight status in the study subjects (% of subjects) in the placebo, CMC/CA 2.25 g and CMC/CA 3.75 g groups.

Figure 5:
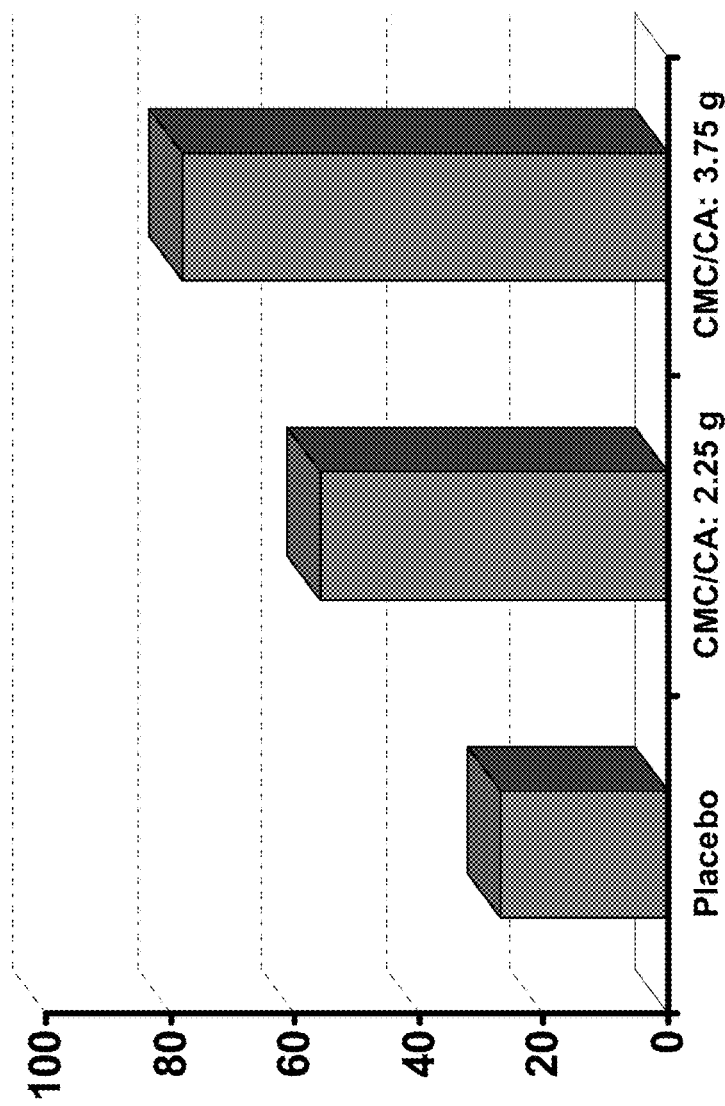
FIG. 5 is a graph showing conversion of impaired fasting blood glucose status to normal fasting blood glucose status (% of subjects) in the placebo (n=11), CMC/CA 2.25 g (n=9) and CMC/CA 3.75 g (n=9) groups over the course of the study described in Example 2.

FIGS. 5-8 and the data in Tables 6 and 7 illustrate the effect of treatment with CMC/CA on glycemic control and markers of diabetes and prediabetes. FIG. 5 shows the

TABLE 7

| | Number of Subjects | | |
|---|---|---|---|
| Glucose Status | Placebo (n = 42) | CMC/CA 2.25 g (n = 41) | CMC/CA 3.75 g (n = 39) |
| Impaired glucose (baseline) | 11 (26%) | 9 (22%) | 9 (23%) |
| Impaired glucose (end of study) | 12 (29%) | 5 (12%) | 3 (8%) |
| Conversion of normal glucose to impaired glucose (end of study) | 4 (10%) | 1 (2%) | 2 (5%) |
| Conversion of impaired glucose to diabetic glucose (end of study) | 0 | 0 | 1 (3%) |
| Conversion of impaired glucose to normal glucose (end of study) | 3 (7%) | 5 (12%) | 7 (18%) |

Figure 9:
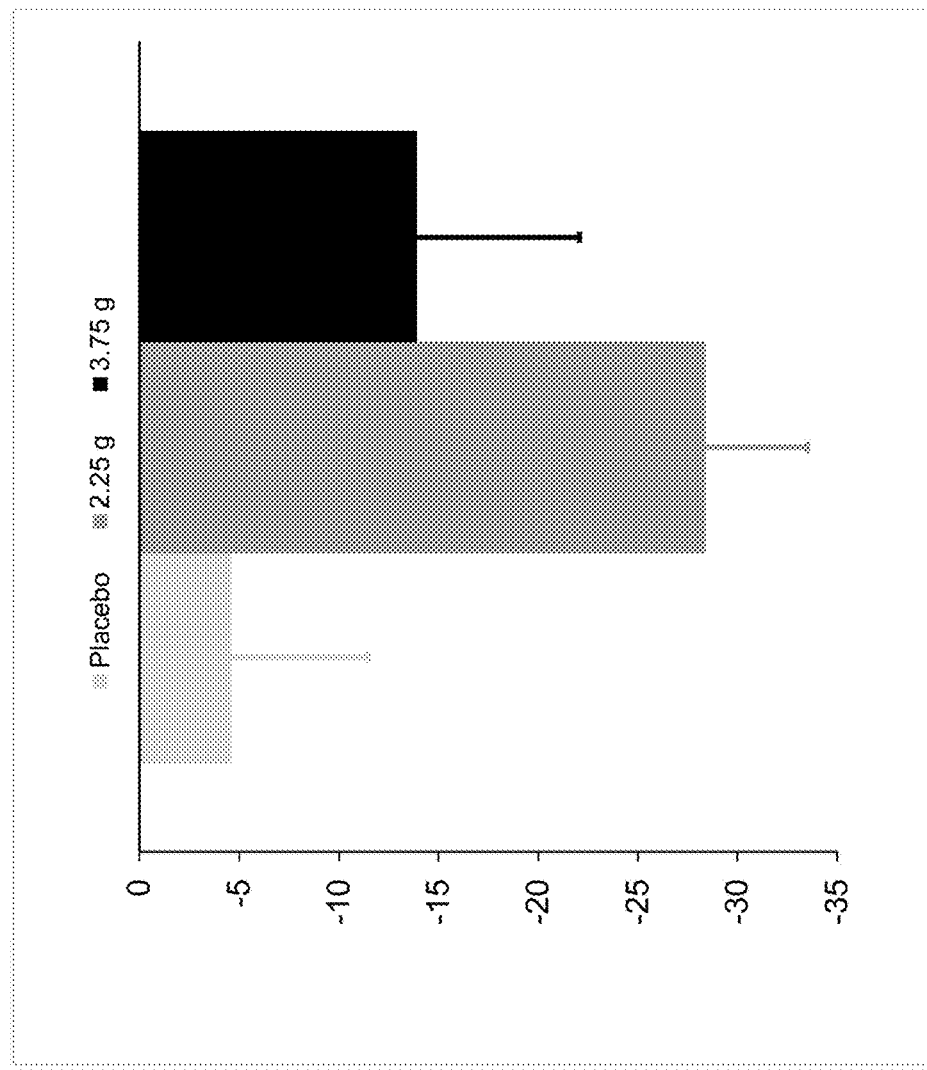
FIG. 9 is a graph showing the change in total energy intake (change from baseline, %, mean±SEM) in subjects with elevated fasting blood glucose (>93 mg/dL) at baseline in the placebo (n=21), 2.25 g CMC/CA (n=21) and 3.75 g CMC/CA (n=14) groups over the course of the study described in Example 2.
Figure 10:
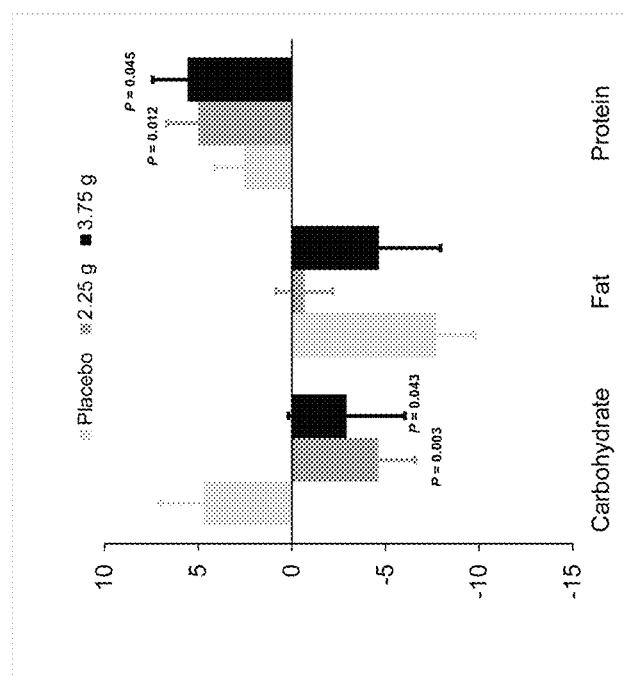
FIG. 10 is a graph showing the change in energy intake from carbohydrate, fat and protein (change from baseline, %, mean±SEM) in subjects with elevated fasting blood glucose (>93 mg/dL) at baseline in the placebo (n=21), 2.25 g CMC/CA (n=21) and 3.75 g CMC/CA (n=14) groups over the course of the study described in Example 2.

FIGS. 9 and 10 illustrate the effect of treatment on energy intake in subjects with elevated fasting blood glucose at baseline. FIG. 9 shows the change in total energy intake in the placebo, CMC/CA 2.25 g and CMC/CA 3.75 g groups. Total energy intake decreased in both CMC/CA groups compared to placebo, with the greatest decrease shown in the CMC/CA 2.25 g group. FIG. 10 shows the change in energy intake from carbohydrate, fat and protein in the placebo, CMC/CA 2.25 g and CMC/CA 3.75 g groups. Energy intake from carbohydrate decreased in both CMC/CA groups, but increased in the placebo group. Energy intake from fat decreased in all groups, while energy from protein increased more in the CMC/CA groups than in the placebo group.

Both doses of CMC/CA were found to be safe and the 2.25 g dose was very well tolerated.

While this invention has been particularly shown and described with references to preferred embodiments thereof, it will be understood by those skilled in the art that various changes in form and details may be made therein without departing from the scope of the invention encompassed by the appended claims.

We claim:

1. A method for treating overweight or obesity in a subject in need thereof, wherein the subject has a fasting blood glucose level of 90 mg/dL, or higher: said method comprising the steps of:
   (a) orally administering to the subject from about 1.5 g to about 3 g of a crosslinked carboxymethylcellulose; and
   (b) orally administering to the subject at least 100 mL water per gram of the crosslinked carboxymethylcellulose,
   wherein said steps (a) and (b) are conducted prior to or with a meal, wherein the carboxymethylcellulose is crosslinked with citric acid and is characterized by:
   (a) a tapped density of at least about 0.6 g/mL;
   (b) an elastic modulus of at least about 350 Pa, and
   (c) a media uptake ratio of at least about 50 in a 1:8 mixture of simulated gastric fluid and water.

2. The method of claim 1, wherein the amount of crosslinked carboxymethylcellulose administered step (a) is from about 1.75 g to about 2.75 g.

3. The method of claim 2, wherein the amount of crosslinked carboxymethylcellulose administered in step (a) is about 2.25 g.

4. The method of claim 1, wherein the subject has a body mass index of 30 or higher.

5. The method of claim 1, wherein the subject has a fasting blood glucose level of 93 mg/dL or higher.

6. The method of claim 1, wherein the subject has a fasting blood glucose level of 95 mg/dL or higher.

7. The method of claim 1, wherein the subject has a fasting blood glucose level in the range of 100 to 125.9 mg/dL.

8. The method of claim 1, wherein the subject has a fasting blood glucose level from 90 to 125.9 mg/dL.

9. The method of claim 1, wherein the amount of water administered in step (b) is at least about 125 mL per gram of crosslinked carboxymethylcellulose.

10. The method of claim 1, wherein the amount of water administered in step (b) is at least about 150 mL per gram of crosslinked carboxymethylcellulose.

11. The method of claim 1, wherein the water content of the crosslinked carboxymethylcellulose is 10% wt/wt or less.

12. The method of claim 1, wherein the crosslinked carboxymethylcellulose is produced by a method comprising the steps of:
   (a) providing a solution of carboxymethylcellulose sodium salt and citric acid in water, said solution consisting essentially of about 5% to about 7% carboxymethylcellulose by weight relative to the weight of the water and citric add in an amount of about 0.15% to about 0.35% by weight relative to the weight of the carboxymethylcellulose;
   (b) maintaining the solution at a temperature from about 40° C. to about 80° C., to evaporate the water and form a substantially dry solid residue;
   (c) grinding the residue to form residue particles; and
   (d) heating the residue particles to a temperature from about 80° C. to about 150° C. for a period of time sufficient to crosslink the carboxymethylcellulose.

* * * * *